United States Patent [19]

Keown et al.

[11] Patent Number: 5,624,947

[45] Date of Patent: Apr. 29, 1997

[54] PHENYL DERIVATIVES USEFUL AS TACHYKININ ANTAGONISTS

[75] Inventors: Linda E. Keown, Cambridge, Great Britain; Tamara Ladduwahetty, London, England; Monique B. Van Niel, Welwyn Garden City, Netherlands

[73] Assignee: Merck, Sharp & Dohme Ltd., Hoddesdon, England

[21] Appl. No.: 481,503

[22] PCT Filed: Dec. 15, 1993

[86] PCT No.: PCT/GB93/02559

§ 371 Date: Jun. 20, 1995

§ 102(e) Date: Jun. 20, 1995

[87] PCT Pub. No.: WO94/14767

PCT Pub. Date: Jul. 7, 1994

[30] Foreign Application Priority Data

Dec. 21, 1992 [GB] United Kingdom ............... 9226581

[51] Int. Cl.$^6$ ............... A61K 31/415; C07D 233/88; C07D 233/91
[52] U.S. Cl. ............... 514/392; 548/327.5; 548/331.5; 514/398
[58] Field of Search ............... 548/327.5, 331.5; 514/392

[56] References Cited

U.S. PATENT DOCUMENTS

| 2,928,835 | 3/1960 | Jacob et al. |
| 3,717,655 | 2/1973 | Godefroi et al. ............... 548/341.1 |
| 5,461,068 | 10/1995 | Thaler et al. ............... 548/341.1 |

FOREIGN PATENT DOCUMENTS

| 0522808A2 | 3/1992 | European Pat. Off. |
| 0499313A1 | 4/1992 | European Pat. Off. |
| 0520555A1 | 6/1992 | European Pat. Off. |
| WO93/24465 | 9/1993 | WIPO |

*Primary Examiner*—Robert W. Ramsuer
*Attorney, Agent, or Firm*—Robert J. North; Melvin Winokur

[57] ABSTRACT

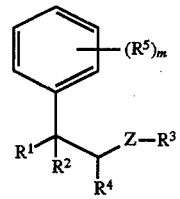

Compounds of formula (I), or a salt or prodrug thereof are tachykinin antagonists.

8 Claims, No Drawings

PHENYL DERIVATIVES USEFUL AS TACHYKININ ANTAGONISTS

This invention relates to a class of aromatic compounds which are useful as tachykinin antagonists. More particularly, the compounds of the invention contain a phenyl moiety and hydroxyl or ether moiety.

The tachykinins are a group of naturally occurring peptides found widely distributed throughout mammalian tissues, both within the central nervous system and in peripheral nervous and circulatory systems.

The structures of three known mammalian tachykinins are as follows: Substance P:
Arg-Pro-Lys-Pro-Gln-Gln-Phe-Phe-Gly-Leu-Met-$NH_2$
Neurokinin A:
His-Lys-Thr-Asp-Ser-Phe-Val-Gly-Leu-Met-$NH_2$
Neurokinin B:
Asp-Met-His-Asp-Phe-Phe-Val-Gly-Leu-Met-$NH_2$ For example, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, Nov. 11, 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis, and fibrositis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9] vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al Science (1990) 250, 279–82] in senile dementia of the Alzheimer type, Alzheimer's disease and Downs Syndrome. Substance P may also play a role in demyelinating diseases such as multiple sclerosis and amyotrophic lateral sclerosis [J. Luber-Narod et. al., poster to be presented at C. I. N. P. XVIIIth Congress, 28th June-2nd July, 1992, in press], and in disorders of bladder function such as bladder detrusor hyper-reftexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), opthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

We have now found a class of non-peptides which are potent antagonists of tachykinin.

The present invention provides a compound of formula (I), or a salt or prodrug thereof:

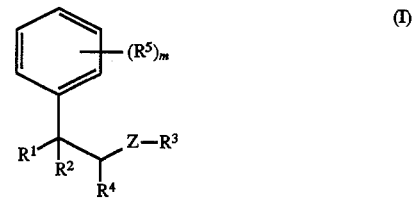

wherein
$R^1$ represents a nitrogen containing aromatic or non-aromatic heterocycle optionally substituted by one or more groups selected from $C_{1-6}$alkyl, $C_{1-6}$alkoxy, oxo, thioxo, halo, trifluoromethyl, nitro, $NR^aR^b$, $NR^aCOR^b$, $CONR^aR^b$, $CO_2R^a$, $SO_2R^a$ and $CH_2OR^a$, where $R^a$ and $R^b$ each independently represent H, $C_{1-6}$alkyl or phenyl optionally substituted by $C_{1-6}$alkyl, halo or trifluoromethyl;

$R^2$ represents H, $C_{1-6}$alkyl or $C_{2-6}$alkenyl;

$R^3$ represents $C_{1-3}$alkyl substituted by a phenyl group which may itself optionally be substituted by one or more of $C_{1-6}$alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ and $CONR^cR^d$;

$R^4$ represents H, $C_{1-6}$alkyl or $C_{2-6}$alkenyl;

each $R^5$ independently represents $C_{1-6}$alkyl, $C_{1-6}$alkoxy, halo or trifluoromethyl;

Z represents O or S; and m represents 0, 1, 2 or 3.

The alkyl, alkenyl and alkynyl groups referred to with respect to any of the formulae herein may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

For phenylalkyl substituents, the alkyl moiety may be straight or branched.

The term "halo" as used herein includes fluoro, chloro, bromo and iodo.

Aptly $R^1$ represents an optionally substituted aromatic heterocycle.

The nitrogen containing aromatic heterocycle represented by $R^1$ may be, for example, a 5- or 6-membered heterocycle and may contain, in addition to the nitrogen atom, one or more heteroatoms selected from O, S and N, or groups $NR^8$ where $R^8$ is H or $C_{1-6}$alkyl.

Suitably $R^1$ represents an optionally substituted 5-membered heteroaryl moiety selected from pyrrolyl, triazolyl, tetrazolyl, thiazolyl, oxazolyl, oxadiazolyl, thiadiazolyl, isoxazolyl, isothiazolyl and imidazolyl. Preferably $R^1$ represents optionally substituted pyrrolyl or imidazolyl. More preferably $R^1$ represents imidazolyl substituted by a nitro or an amino group.

Aptly R¹ represents an optionally substituted non-aromatic heterocycle.

Suitably R¹ represents a 4, 5, 6, 7 or 8 membered ring which may have one heteroatom in addition to the nitrogen atom, for example an oxygen atom. Apt groups include those of the formula

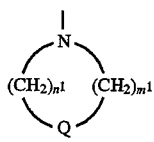

wherein Q is CH$_2$, NR$^8$ where R$^8$ is as hereinbefore defined, O or S, n$^1$ is 1, 2 or 3 and m$^1$ is 1 or 2 with the proviso that when Q is NR$^8$, O or S neither n$^1$ nor m$^1$ is 1; which group can be optionally substituted by one or two oxo groups or C$_{1-6}$ alkyl groups.

A favoured non-aromatic group R$^1$ is morpholino.

R$^1$ is linked to carbon atom which also bears the R$^2$ group and the other groups shown in formula (I) via the nitrogen atom.

Suitable values for the groups R$^2$ and R$^4$ include R and methyl, preferably H.

Suitably R$^3$ represents a C$_{1-6}$ alkyl chain bearing a substituent which is a substituted phenyl group. Suitable phenyl substituents include methyl, methoxy, nitro, cyano, halo and trifluorometyl. Preferably R$^3$ represents methyl substituted by a substituted phenyl group. Preferably one or two substituents will be present in the phenyl ring. More preferably R$^3$ represents methyl substituted by 3,5-disubstituted phenyl, such as 3,5-dimethylphenyl or 3,5-bistrifluoromethylphenyl.

Preferably m represents zero.

A preferred sub-class of compounds according to the invention is represented by formula (Ia):

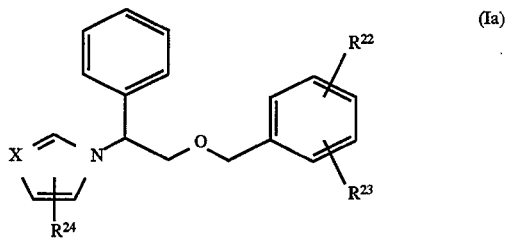

(Ia)

wherein

X is N or CH;

R$^{22}$ and R$^{23}$ each independently represent H, C$_{1-6}$ alkyl, C$_{2-6}$ alkenyl, C$_{1-6}$alkoxy, halo, cyano, nitro, trifluoromethyl, trimethylsilyl, hydroxy, phenoxy or amino;

R$^{24}$ is NO$_2$ or NH$_2$, and may be located at any available ring position; and salts and prodrugs thereof.

Specific compounds within the scope of the present invention include:

(+)-1-[3,5-(bistrifluoromethylphenyl)methyloxy]-2-N(2,5-dimethylpyrrole)-2-phenylethane;

1-[3,5-(bistrifluoromethylphenyl)methyloxy]-2-N (imidazole)-2-phenylethane;

(±)-1-[3,5-(bistrifluoromethylphenyl)methyloxy]-2-N(2-nitroimidazole)-2-phenylethane;

(±)-2-N(2-aminoimidazole)-1-[3,5-(bistrifluoromethylphenyl)methyloxy]-2-phenylethane;

(±)-1-[3,5-(bistrifluoromethylphenyl)methyloxy]-2-N(4-nitroimidazole)-2-phenylethane;

(±)-1-[3,5-(bistrifluoromethylphenyl)methyloxy]2-N-morpholino-2-phenylethane;

(±)-1-[3,5-(bistrifluoromethylphenyl)methyloxy]2-N-(piperidine-2,6-clione-2-phenylethane and salts and prodrugs thereof especially the pharmaceutically acceptable salts-thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The present invention includes within its scope solvates of the compounds of formula (I) and, salts thereof, for example, hydrates.

The compounds according to the invention have at least one asymmetric centre, and may accordingly exist both as enantiomers and as diastereoisomers. It is to be understood that all such isomers and mixtures thereof are encompassed within the scope of the present invention.

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous-system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy. According to a further or alternative aspect, the present invention provides a compound of formula (I) for use in the manufacture of a medicament for the treatment of physiological disorders associated-with an excess of tachykinins, especially substance P. The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention may be prepared from compounds of formula (II)

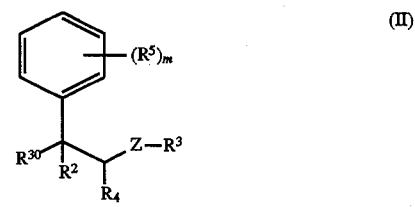

(II)

wherein $R^2$, $R^3$, $R^4$, $R^5$, Z and m are as defined for formula (I) above and $R^{30}$ represents a leaving group, by reation with a metallated aromatic heterocycle of formula $R^1$-M wherein $R^1$ is as defined for formula (I) and M represents a metal, such as an alkai metal, for example sodium or lithium, or with an non-aromatic amine $R^1$-H, optionally in the presence of a tertiary amine base.

Suitable leaving groups represented by $R^{30}$ include aryl and alkyl sulphonate groups, such as tosylate and mesylate groups.

The reaction is conveniently effected in a suitable organic solvent, such as dimethyl formamide, or an ether, such as, for example, tetrahydrofuran, or a mixture thereof, suitably at room temperature.

Alternatively, compounds of formula (I) may be prepared from compounds of formula (III)

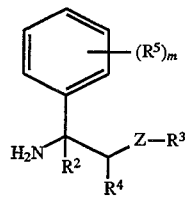
(III)

wherein $R^2$, $R^3$, $R^4$, $R^5$, Z and m are defined for formula (I) using conventional methods for the construction of the heteroaromatic ring. Suitable methods are described, for example, in Comprehensive Heterocyclic Chemistry, Katritzky and Rees, Pergamon Press, 1984.

Compounds of formula (I) may also be prepared from other compounds of formula (I) by interconversion processes. Such processes are particularly useful for modifying substituents in the heteroaromatic ring. For example, compounds of formula (I) wherein $R^1$ represents a heteroaryl moiety substituted by an amino group may be prepared from the corresponding compounds of formula (I) wherein $R^1$ represents the same heteroaryl moiety substituted by a nitro group, by reduction. Further suitable interconversion procedures will be readily apparent to those skilled in the art.

Compounds of formula (II) may be prepared from intermediates of formula (IV)

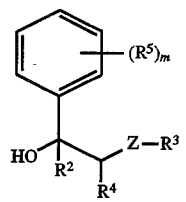
(IV)

wherein $R^2$, $R^3$, $R^4$, $R^5$, Z and m are as defined for formula (I), by conversion of the hydroxy group to a leaving group under conventional conditions, for example, by reaction with a compound of formula $R^{30}$-Hal, where Hal represents halo, such as chloro or bromo, in the presence of a base.

Suitable bases of use in the reaction include tertiary amines such as, for example, triethylamine.

The reaction is conveniently effected in a suitable organic solvent, such as an ether, for example diethyl ether.

Intermediates of formula (IV) may be prepared by reaction of compounds of formula (V) with compounds of formula (VI)

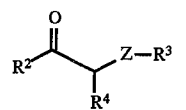
(V)

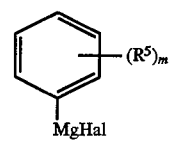
(VI)

wherein $R^2$, $R^3$, $R^4$, $R^5$, Z, m and Hal are as previously defined.

The reaction is conveniently effected in a suitable organic solvent, such as an ether, for example diethyl ether.

Compounds of formula (V) may be Prepared by reaction of a compound of formula (VII), or an appropriately protected derivative thereof, with a compound of formula (VIII)

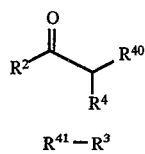
(VII)

$R^{41}$—$R^3$ (VIII)

Wherein $R^2$ $R^3$ and $R^4$ are as previously defined, one of $R^{40}$ and $R^{41}$ represents ZH where Z is as previously defined and the other of $R^{40}$ and $R^{41}$ represents a leaving group, in the presence of a base, followed by deprotection, if required.

Suitably $R^{40}$ represents ZH and $R^{41}$ represents a leaving group.

Suitable leaving groups include halo, e.g. chloro, bromo or iodo, or sulphonate derivatives such as tosylate or mesylate.

The reaction is conveniently carried out in a suitable organic solvent, such as dimethylformamide, at a temperature in the region of 0° C. Favoured bases of use in the reaction include alkali metal hydrides, such as sodium hydride.

The intermediates of formula (VII) above wherein $R^{40}$ is SH may be prepared from the corresponding intermediates of formula (VII) wherein $R^{40}$ represents OH by treating the latter compound with hydrogen sulphide in the presence of aluminium oxide, as described by Lucien et al., *Nouveau J. Chem.*, 3, 15 (1979), or phosphorus pentasulphide in a suitable solvent, e.g. pyridine, at ambient or elevated temperatures, suitably at reflux temperature.

Intermediates of formula (VII) wherein $R^{40}$ is a leaving group may be prepared form intermediates of formula (VII) wherein $R^{40}$ represents OH as described for the preparation of compounds of formula (II) from compounds of formula (IV) above.

Intermediates of formula (VII) wherein $R^{40}$ is OH are commercially available or may be prepared from commercially available starting materials by conventional procedures which will be readily apparent to those skilled in the art.

Intermediates of formula (III) may be prepared from compounds of formula (IX)

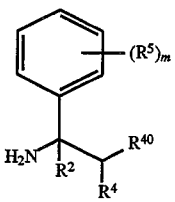
(IX)

wherein $R^2$, $R^4$, $R^5$, $R^{40}$ and m are as previously defined by reaction with compounds of formula (VIII) as previously defined, in the presence of a base, as described for the preparation of compounds of formula (V) above.

Compounds of formula (IX) wherein $R^{40}$ is SH or a leaving group may be prepared from compounds of formula (IX) wherein $R^{40}$ is OH analogously to the preparation of compounds of formula (VII) wherein $R^{40}$ is SH or a leaving group.

Compounds of formula (IX) wherein $R^4$ is H and $R^{40}$ is OH may be prepared from compounds of formula (X)

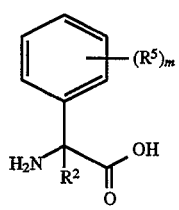

wherein $R^2$, $R^5$ and m are as previously defined, or alkyl esters thereof, by reduction.

Suitable reducing agents include metal hydrides, such as lithium aluminium hydride. The reaction is conveniently effected in a suitable organic solvent such as ether, for example, tetrahydrofuran, suitably at elevated temperature, such as the reflux temperature of the solvent.

Compounds of formula (X) are commercially available or may be prepared by conventional procedures for the preparation of amino acids which are well documented and are described, for example, in *Chemistry and Biochemistry of the Amino Acids*, ed. G. C. Barrett, Chapman and Hall, 1985.

Compounds of formula (IX) wherein $R^{40}$ is OH and $R^4$ is other than H may be prepared from intermediates of formula (XI)

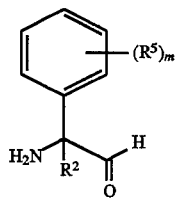

wherein $R^2$, $R^5$ and m are as defined for formula (I), by reaction with an organometallic reagent of formula $MR^4$, wherein $R^4$ is as previously defined and M represents a metal, such as lithium, or a metal halide, such as a magnesium halide, e.g. magnesium chloride or magnesium bromide.

The reaction is suitably effected in an inert organic solvent such as an ether, for example, diethylether or tetrahydrofuran.

Aldehydes of formula (XI) may be prepared by reduction of esters of compounds of formula (X) using diisobutylaluminium hydride.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, compounds of formula (I) wherein $R^1$ is H may be resolved into their component enantiomers by standard techniques, such as the formation of diastereomeric esters or amides, followed by chromatographic separation and removal of the chiral auxiliary. These compounds-can then be used to make individual enantiomers of compounds of formula (I) wherein $R^1$ is other than H.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

(+)-1[(3,5-Bistrifluoromethylphenyl)methyloxy]-2-N (2,5-dimethyl pyrrole)-2-phenyl ethane a) L-2-Phenylglycinol (5 g) and di-t-butyldicarbonate (9.4 g) was stirred in a dichloromethane solution (30 ml) at room temperature for 3 hours. The precipitate which formed was filtered to give N-t-butoxycarbonyl-L-2-phenylglycinol, 4 g.

b) To a solution of 2-N-t-butoxycarbonylamino-L-2-phenylglycinol (23.7 g; Example 1a) and 3,5-bis (trifluoromethyl)benzyl bromide (33.8 g) dissolved in dimethylformamide (75 ml) was added sodium hydride (80% suspension in oil, 3.3 g) in portions over 30 minutes. After stirring the solution at ambient temperature for 1 h, water (500 ml) and ethyl acetate (500 ml) were added. The organic phase was washed further with water (2×100 ml), saturated brine and dried ($MgSO_4$). After evaporation in vacuo the residue was chromatographed on silica (eluting with 5% ethyl acetate in petroleum ether bp 60°–80° C.) to give (S)-1-(3,5-bis(trifluoromethyl)phenyl)methyloxy)-2-N-t-butoxycarbonylamino-2-phenylethane, m.p. 53°–54° C.

c) The product of Example 1b (10 g) was allowed to stand in 250 ml of diethyl ether saturated with gaseous HCl. The solvent was removed in vacuo and the residue recrystallised from diethyl ether-petroleum ether to give crystalline (+)-2-ammonium-1-(bistrifluoromethylphenyl)methyloxy-2-phenyl ethane, hydrochloride salt.

d) To a solution of(+)-2-ammonium-1-(bistrifluoromethylphenyl)methyloxy-2-phenyl ethane, hydrochloride salt (1 mmol) and 1.1 equivalents of 2,5-hexanedione in 5ml methanol was added potassium hydroxide (1.5 mmol). The reaction was refluxed for 48 h and partitioned between dichloromethane-water. The organic phase was separated, dried ($MgSO_4$), concentrated in vacuo, and poured through a plug of silica using 5% ethyl acetate-pet. ether as eluent. The flitrate was concentrated to give the title compound as a clear oil: ($CDCl_3$) $\delta 2.05$ (6H, s), 4.1–4.15 (1H, m), 4.4–4.45 (1H, m), 4.5–4.7 (2H, m), 5.6–5.65 (1H, m), 5.8 (2H, s), 7.1–7.15 (2H, m), 7.2–7.4 (3H, m), 7.7 (2H, s), 7.8 (1H, s); Found: C, 62.43; H, 4.83; N, 3.32. $C_{23}H_{21}NOF_6$ requires: C, 62.58; H, 4.79; N, 3.17.

EXAMPLE 2

1-[(3,5-Bistrifluoromethylphenyl)methyloxy]2-N (imidazole)-2-phenyl ethane a) To a stirred solution of solketal (0.151 mol) in DMF/THF (1:1, 300 ml) under a nitrogen atmosphere was added sodium hydride (1.2 equivalents of an 80% dispersion in mineral oil). The anion was allowed to form over one hour prior to addition of 3,5-bistrifluoromethylbenzyl bromide. The reaction was partitioned between ethyl acetate-saturated ammonium chloride after 1 h and the organic phase separated, dried ($MgSO_4$), and concentrated to a yellow oil. Chromatography using pet. ether then 20% ethyl acetate-pet. ether as eluent gave 2,2-dimethyl- 1,3-dioxolane-4-methanol-3,5-bistrifluoromethylbenzyl ether as a yellow oil: ($CDCl_3$) $\delta 1.4$ (3H, s), 1.45 (3H, s), 3.6–3.65 (2H, m), 3.7–3.8 (1H, m), 4.1–4.15 (1H, m), 4.3–4.4 (1H, m), 4.7 (2H, s), 7.8 (3H, s).

b) The product from a) above was dissolved in 150 ml THF and allowed to stand for 18 h with 30 ml 2N hydrochloric acid. THF was removed in vacuo and the residue partitioned between ethyl acetate and saturated sodium carbonate solution. The organic phase was separated, dried (MgSO$_4$) and concentrated to give 1-glyeerol-(3,5-bistrifluorobenzyl)ether as a yellow oil: (CDCl$_3$) δ2.0 (1H, s), 2.6 (1H, s), 3.6–3.7 (3H, m), 3.7–3.8 (1H, m), 3.9–4.0 (1H, m), 4.7 (2H, s), 7.8 (2H, s), 7.85 (1H, s).

c) A solution of the diol from b) above in 200 ml dichloromethane was cooled in an ice-water bath, and treated with a solution of 1.1 equivalents sodium metaperiodate in 100 ml water. A further 1 g of sodium metaperiodate was added after 3 h. The reaction was allowed to stand for 48 h, the dichloromethane layer separated, dried (MgSO$_4$), concentrated in vacuo and purified by chromatography using 20% ethyl acetate-pet. ether as eluent, to give [(3,5-bistrifluoromethylphenyl)methyloxy]ethanol as a clear oil. Bp. 94° C./1.31 mBar.

d) To a stirred solution of the aldehyde (3.3 mmol) from c) above in 5 ml anhydrous diethyl ether under a nitrogen atmosphere was added phenylmagnesium bromide (3.0M solution in diethyl ether, 1.3 ml). The reaction was partitioned between ethyl acetate-saturated ammonium chloride after 2 h. The organic phase was separated, dried (MgSO$_4$), concentrated and chromatographed using 20% ethyl acetate-pet. ether as eluent, to give 1-[(3,5-bistrifluoromethylphenyl)methyloxy]-2-hydroxy-2-phenyl ethane as a clear oil. (CDCl$_3$) δ3.6–3.8 (2H, m), 4.7 (2H, s), 4.95–5.05 (1H, m), 7.2–7.4 (5H, m), 7.7–7.8 (2H, m).

e) A solution of the alcohol (6.9 mmol) from d) above in 5 ml diethyl ether was treated with triethylamine (1.44 ml) followed by methanesulphonyl chloride (0.8 ml). The reaction was stirred for 2 h then partitioned between ethyl acetate-water. The organic phase was separated, dried (MgSO$_4$) and concentrated to a yellow oil. Purification by chromatography using 10% ethyl acetate-pet. ether as eluent gave the mesylate as a pale yellow oil.

f) A mixture of the mesylate (0.7 mmol) from e) above and 1.2 equivalents of the sodium salt of imidazole in 4 ml DMF/THF (1:1) was allowed to stand overnight. The reaction was partitioned between diethyl ether-water, the organic phase separated, dried (MgSO$_4$), concentrated in vacuo and purified by chromatography using 20% ethyl acetate-pet. ether as eluent to afford the title compound as a clear oil: (CDCl$_3$) δ4.1–4.15 (2H, m), 4.6–4.7 (2H, m), 5.4–5.45 (1H, m), 7.0 (1H, s), 7.1 (1H, s), 7.15–7.2 (2H, m), 7.3–7.4 (3H, m), 7.6–7.65 (3H, m), 7.8 (1H, s).

EXAMPLE 3

(±)- 1-[(3,5-Bistrifluoromethylphenyl)methyloxy]-2-N(2-nitroimadazole-2-phenyl ethane A suspension of 2-nitroimidazole (2.5 mmol) in 3 ml anhydrous THF was stirred under nitrogen and treated with sodium hydride (1.1 equivalents of an 80% dispersion in oil). The anion was allowed to form over 2 h prior to being reacted in an analogous manner described in Example 2 to give the title compound as a yellow oil. (CDCl$_3$) δ4.1–4.2 (2H, m), 4.6–4.8 (2H, m), 6.5–6.6 (1H, m), 7.1–7.4 (7H, m), 7.6 (2H, s), 7.8 (1H, s)

EXAMPLE 4

(±)-2N(2-aminoimidazole)-1[(3,5-bistrifluoromethylphenyl) methyloxy)]-2-phenyl ethane 1-[(3,5-bistrifluoromethylphenyl)methyloxy]-2-N(2-nitroim idazole)-2-phenyl ethane (Example 3) (60 mg) was dissolved in 10 ml methanol and was hydrogenolysed over 100 mg Pd/C at 50 psi for 3 h. The catalyst was removed by filtration, the filtrate concentrated in vacuo and purified by chromatography using methanol-ethyl acetate as eluent, to give the title compound as an oil. (CDCl$_3$) δ4.0–4.2 (4H, m), 4.6–4.7 (2H, m), 5.3–5.4 (1H, m), 6.6–6.7 (2H, m), 7.2–7.4 (5H, m), 7.7 (2H, s), 7.8 (1H, s).

EXAMPLE 5

(±)-1-[(3,5-Bistrifluoromethylphenyl)methyloxy]-2-N(4-nitroimidazole)-2-phenyl ethane The title compound was prepared in an analogous manner to that described in Example 3 using 4-nitroimidazole (6.6 mmol): (CDCl$_3$) δ4.1–4.2 (2H, m), 4.7 (2H, s), 5.2–5.3 (1H, m), 7.2–7.3 (2H, m), 7.4–7.45 (3H, m), 7.55 (1H, s), 7.6 (2H, s), 7.8 (2H, 2).

EXAMPLE 6

(±)-1-[(3,5-Bistrifluoromethylphenyl)methyloxy]-2-N-morpholino-2-phenyl ethane hydrochloride salt A solution of 2,5-dihydrofuran (0.11 ml) in methanol (10 ml) was cooled to –78° C. Ozone gas was bubbled through the solution until a blue colouration developed. The mixture was flushed with nitrogen and then sodium cyanoborohydride (0.22 g) was added. After stirring at –78° C. for 10 minutes, a solution of 1-[3,5-bistrifluoromethylphenyl) methyloxy-2-amino-2-phenyl ethane in methanol (8 ml) was added dropwise and the reaction mixture stirred at 0° C. for 3 h. The reaction was quenched by addition of acetic acid, and solvent was removed in vacuo. 10% Sodium hydroxide solution was added to the residue and the product extracted into dichloromethane (×3). The combined organics were washed with brine, dried (MgSO$_4$) and concentrated in vacuo. The product was purified by chromatography on silica using 20%→30%→40% ethyl acetate in petrol as eluent. The product was dissolved in diethyl ether and a methanolic solution of hydrogen chloride was added. Solvent was removed in vacuo and the title comnound obtained by trituration with diethyl ether. MS (CI$^+$) m/z 434 ((M+1) $^+$100%).

EXAMPLE 7

(±)-1-[(3,5-Bitrifluoromethylphenyl)methyloxy]-2-N-(piperidine-2,6-dione-2-phenyl ethane A solution of 1-[3,5-bistrifluoromethylphenyl) methyloxy-2-amino-2-phenyl ethane (0.28 g) in toluene (5 ml) was added to a solution of glutaric anhydride (0.088 g) in toluene (10 ml) and the reaction mixture heated at reflux for 20 h. Solvent was removed in vacuo and the crude material purified by chromatography on silica using 15% ethyl acetate in petrol as eluent. The title compound was recrystallised from ethyl acetate-petrol. MS (CI$^+$) m/z 460 ((M+1)$^+$80% ).

We claim:

1. A compound of formula (I), or a pharmaceutically acceptable salt or prodrug thereof:

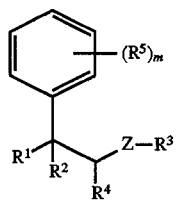

wherein

R¹ is imidazoyl nitro, NR$^a$R$^b$ and NR$^a$COR$^b$, where R$^a$ and R$^b$ each independently represent H, $C_{1-6}$alkyl or phenyl optionally substituted by $C_{1-6}$alkyl, halo or trifluoromethyl;

R² represents H, $C_{1-6}$alkyl or $C_{2-6}$alkenyl;

R³ represents $C_{1-3}$alkyl substituted by a phenyl group which may itself optionally be substituted by one or more of $C_{1-6}$alkyl, $C_{2-6}$ alkenyl, $C_{2-6}$ alkynyl, halo, cyano, nitro, trifluoromethyl and trimethylsilyl;

R⁴ represents H, $C_{1-6}$alkyl or $C_{2-6}$alkenyl;

each R⁵ independently represents $C_{1-6}$alkyl, $C_{1-6}$alkoxy, halo or trifluoromethyl;

Z represents O or S; and m represents 0, 1, 2 or 3.

2. A compound according to claim 1 wherein R¹ is 5-imidazolyl substituted by a nitro or amino group.

3. A compound according to claim 1 wherein R² and R⁴ are hydrogen or methyl.

4. A compound according to claim 1 wherein R³ is $C_{1-3}$ alkyl substituted by a phenyl group bearing 1 or 2 substituents on the phenyl ring.

5. A compound according to claim 4 wherein R³ is methyl substituted by 3, 5-disubstituted phenyl.

6. A compound selected from (±) -1- [3,5-(bistrifluoromethylphenyl)methyloxy]-2-N(2-nitroimidazole)-2-phenylethane; (±)-2-N(2-aminoimidazole)-1-[3,5-(bistrifluoromethylphenyl) methyloxy]-2-phenylethane; (±)-1-[3,5-(bistrifluoromethylphenyl)methyloxy]-2-N(4-nitroimidazole)-2-phenylethane; and salts and prodrugs thereof.

7. A pharmaceutical composition comprising one or more compounds of formula (I) as in claim 1 in association with a pharmaceutically acceptable carrier.

8. A method of treatment of physiological disorder associated with an excess of tachykinin which method comprises administration to a patient in need thereof of a tachykinin reducing amount of a compound of formula (I) or a composition comprising a compound of formula (I) as defined in any one of claims 1, 4, 6 or 7.

* * * * *